United States Patent [19]
Mertins et al.

[11] Patent Number: 5,938,439
[45] Date of Patent: Aug. 17, 1999

[54] SYRINGE FOR DISPENSING VISCOUS MATERIAL AND METHOD

[75] Inventors: Jürgen Mertins, Gams, Switzerland; Frank Müller, Feldkirch; Klaus Galehr, Schlins, both of Austria

[73] Assignee: Ivoclar A.G., Schaan, Liechtenstein

[21] Appl. No.: 08/984,360

[22] Filed: Dec. 3, 1997

Related U.S. Application Data

[60] Provisional application No. 60/055,421, Aug. 4, 1997.

[30] Foreign Application Priority Data

Dec. 13, 1996 [DE] Germany ............... 196 51 981

[51] Int. Cl.⁶ .......................................... A61C 5/04
[52] U.S. Cl. ................................... 433/90; 604/218
[58] Field of Search .................. 433/90, 89; 604/59, 604/60, 61, 62, 63, 64, 218, 219, 232, 235

[56] References Cited

U.S. PATENT DOCUMENTS

| | | | |
|---|---|---|---|
| 2,903,794 | 9/1959 | Carfagni | 433/90 |
| 3,854,209 | 12/1974 | Franklin et al. | 433/90 |
| 3,900,954 | 8/1975 | Dragan | 433/90 |
| 4,295,828 | 10/1981 | Rudler | 433/90 |
| 4,391,590 | 7/1983 | Doughterty | 433/90 |
| 4,472,141 | 9/1984 | Dragan | 433/90 |
| 4,801,263 | 1/1989 | Clark | 433/90 |
| 5,078,686 | 1/1992 | Bates | 604/218 |
| 5,484,734 | 1/1996 | Kimura | 436/176 |
| 5,697,918 | 12/1997 | Fischer et al. | 433/90 |

FOREIGN PATENT DOCUMENTS

| | | |
|---|---|---|
| 2 175 021 | 11/1996 | Canada . |
| 0 063 891 A1 | 11/1982 | European Pat. Off. . |
| 298292 | 11/1928 | United Kingdom . |

*Primary Examiner*—John J. Wilson
*Attorney, Agent, or Firm*—John C. Thompson; Alan S. Korman

[57] ABSTRACT

A syringe for dispensing a viscous material has a cylindrical housing with a first and a second end. An outlet member is connected to the first end of the cylindrical housing. A deformable dispensing body is slidable in the cylindrical housing from the second end to the first end for dispensing the viscous material in a dispensing direction of the syringe. The deformable dispensing body is insertable into the outlet member and deformable to the shape of the outlet member, but has a dimensionally stable trailing end.

26 Claims, 1 Drawing Sheet

SYRINGE FOR DISPENSING VISCOUS MATERIAL AND METHOD

This application claims the benefit of U.S. Provisional Application No. 60/055,421, filed Aug. 4, 1997.

BACKGROUND OF THE INVENTION

The present invention relates to a syringe for dispensing viscous materials, comprising an outlet member and a plunger means for dispensing the material from the syringe whereby the dispensing means can be at least partly inserted into the outlet member.

Such a syringe is, for example, known from U.S. Pat. No. 3,900,954.

This syringe is characterized by an especially good utilization of the dental material to be applied. The syringe comprises a dispensing body at the forward end of the plunger of the syringe. the dispensing body has a conically tapering tip which can be introduced into the outlet member so as to displace the dental material as completely as possible.

With such a dispensing body it is possible to reduce the amount of dental material that would otherwise remain within the syringe. However, some material is always retained within the outlet member so that the dental material within the syringe which is, in general, an expensive product, cannot be completely utilized. For example, when a light-curing dental material is used, the dental material over time will cure within the syringe and will plug the outlet member.

In order to prevent such losses of dental material, it has been suggested to shorten the dispensing body and to make it more compact. Since such a syringe is used for applying the filling material in the mouth of a patient, such a construction, however, leads to the problem that not all teeth can be easily reached with the syringe.

For example, from British Patent 298 292 it is known to use a very short and thin outlet member into which a special end piece of the plunger which is comprised of rubber can be introduced. This solution, however, allows only for a comparatively minimal dispensing velocity and the pressure applied onto the viscous material increases with reduction of the flow cross-section of the outlet member. Furthermore, the actuating force due to the friction of the rubber plunger is relatively great, since the plunger is slightly larger than the inner diameter of the housing in order to provide the necessary sealing action. It is not surprising that such rubber plungers have not found ac ceptanoe in practice.

Especially when the outlet member is positioned at an angle relative to the axis of the syringe, the guiding of the dispensing body within the outlet member is unsatisfactory. The forward end is relatively freely movable and has the tendency to cling to a wall when pressure is applied by the plunger. Due to the asymmetric guiding of the dispensing body there is the risk that the dental material can exit laterally relative to the dispensing body. This can result in a soiling of the syringe.

It is therefore an object of the present invention to provide a syringe for viscous materials according to the aforementioned kind and/or a method for manufacturing such a syringe that allows for a reliable and complete dispensing of the used viscous material, especially a dental material.

SUMMARY OF THE INVENTION

A syringe for dispensing a viscous material according to the present invention is primarily characterized by:

a cylindrical housing having a first and a second end;

an outlet member connected to the first end of the cylindrical housing;

a deformable dispensing body slidable in the cylindrical housing from the second end to the first end for dispensing the viscous material in a dispensing direction of the syringe;

the deformable dispensing body at least partly insertable into the outlet member when dispensing the viscous material and deformable to the shape of the outlet member;

the deformable dispensing body having a dimensionally stable trailing end remote from the outlet member.

Advantageously, the syringe further comprises a plunger connected to the trailing end for moving the deformable dispensing body within the cylindrical housing.

The deformable dispensing body is a plunger and has an outer diameter matching the inner diameter of the cylindrical housing. The deformable dispensing body preferably has a leading end for deformable insertion into the outlet member.

The outlet member preferably has an outlet opening. The outlet member tapers conically toward the outlet opening or, in another embodiment of the present invention, the outlet opening has an identical cross-section from the first end of the cylindrical housing to the outlet opening.

The outlet member preferably has a tapering cross-section relative to the cylindrical housing.

Preferably, the syringe further comprises a guide cone, connected between the cylindrical housing and the outlet member, for guiding the deformable dispensing body into the outlet member.

The deformable dispensing body preferably has a volume matching the inner volume of the outlet member and of the guide cone.

Advantageously, the syringe further comprises a plunger for moving the deformable dispensing body within the cylindrical housing. The plunger is preferably fastened to the trailing end of the deformable dispensing body.

The plunger and the deformable dispensing body expediently are in the form of a unitary plastic part, wherein the plunger is formed by curing or cross-linking a portion of the unitary plastic part.

The plunger is preferably glued to the trailing end.

The trailing end comprises a guide disk forming a plunger of the syrnge and providing a seal relative to the cylindrical housing.

Expediently, the deforn rable dispensing body consist of a silicone elastomer or a non-silloone elastomer having a shore hardness of 10 to 90. The shore hardness is preferably 20 to 60.

The deformable dispensing body comprises a pointed tip in a relaxed state thereof, wherein the tapering angle of the pointed tip is greater than the tapering angle of the outlet member.

Preferably, the deformable dispensing body comprises a substantially non-deformable plunger and an elastic part connected to the plunger, wherein the elastic part is insertable into the outlet member for completely dispensing the viscous material from the outlet member.

The elastic part has a radial projection forming a sealing lip relative to the inner diameter of the cylindrical housing.

The outlet member is angularly positioned relative to the cylindrical housing and the deformable dispensing body extends into the outlet member when the syringe is completely emptied.

The outlet member is positioned at an angle of 45° relative to the cylindrical housing.

The deformable dispensing body is a fluid-filled body, preferably filled with a hydrogel.

Advantageously, the syringe further comprises a plunger for moving the deformable dispensing body within the cylindrical housing. The deformable dispensing body is Inserted into the cylindrical housing before inserting the plunger.

The present invention also relates to a syringe according to the inventive embodiment in combination with a viscous material contained in the cylindrical housing.

The present invention further relates to a method for manufacturing a syringe for dispensing viscous material, as disclosed in the present specification, wherein the method comprises the steps of:

injection molding in two steps a first layer and a second layer so as to form the deformable dispensing body, wherein the second layer is more elastic than the first layer; and positioning the deformable dispensing body in the cylindrical housing such that the elastic layer faces the outlet member.

The step of injection molding may further Include forming a sheet of the first and second layers, wherein the method further comprises the step of stamping the deformable dispensing body from the sheet.

Advantageously, the method further comprises the step of cross-linking the deformable dispensing body at one end for hardening the first layer.

The inventive solution allows with surprisingly simple means the complete dispensing of dental material from the outlet member without encountering canting of the plunger, even when the outlet member is slanted, and without impairing the sealing function of the plunger. This holds also true for very narrow outlet members. It is especially favorable that, in essence, the plunger and the dispensing body are combined to form one component whereby the dispensing body due to its elastic deformability can be shaped to any shape of the tip of the outlet member and practically automatically changes its shape upon moving the plunger in the dispensing direction.

Even though a certain dimensional stability of the dispensing body is desirable and aids in completely dispensing the viscous material that sometimes has a very high flexibility, in principal, it is also possible to provide instead of the elastic deformability a plastic deformability as long as it is ensured that the dispensing action, by introduction of the dispensing body into the tip (outlet member), results in the complete removal of the material, especially the dental material.

It is especially favorable when between the cylindrical housing of the syringe and the outlet member a guide cone for the deformation of the dispensing body is provided. This guide cone initiates the deformation of the dispensing body upon moving the plunger into the dispensing direction whereby the abrupt change of the cross-section between the cylindrical part of the syringe and the outlet member is reduced by the guide cone.

It is also advantageous when the dispensing body is deformable such that a forward (leading end) is suitable for at least a partial introduction into the outlet member. Due to its elasticity, a portion of the dispensing body can remain within the cylindrical housing of the syringe in order to fill the space therein while a continuous transition into the outlet member is ensured because of the elasticity of the plastic material used.

It is preferred that the dispensing body extends, when the plunger abuts the forward end of the syringe, into the forward end of the outlet member in order to completely dispense or remove the dental material from the outlet member, especially when a light-curing dental material is contained in the syringe.

Such a complete removal of the dental material is advantageous in regard to the disposal of the syringe since the inventive syringe is then especially suitable for the application of hazardous materials because the expensive disposal of the used syringes as contaminated or hazardous waste can be avoided.

It is understood that the plunger, in a manner known per se, can be activated with a push rod or a threaded spindle and that the design in other respects can be selected as needed. The inventive syringe can be especially applied when a design with an angularly positioned outlet member is required, as is needed for the so-called Cavifils, because the inventive dispensing body is easily laterally deformable.

It is furthermore favorable that the partially higher pressure stress, observed during removal of remaining material from conventional syringes and possibly detrimental to the employed material, can be inventively avoided so that a gentle removal of the material by the elastic plunger Is possible and dead volume can be completely avoided.

In conjunction with conventional filling devices, there is also the advantage that an air bubble free filling of the syringe can be accomplished since, after return of the plunger, a deformation of the dispensing body in the reverse direction takes place without leading to hollow spaces within the syringe.

In order to prevent that dental material can be retained laterally relative to the deformable dispensing body, it is preferred to provide the dispensing body in the relaxed state with a dispensing surface at its front end that is as large as possible. However, it is also possible to provide the front end with a conical shape.

However, it is preferred that the dispensing body be conically deformed only within the guide cone whereby it is preferred in this context that the end of the guide cone at the cylindrical housing is the end stop for the movement of the plunger so that an abutment for the plunger is provided. In this context it is favorable when the inner volume of the outlet member and the guide cone is substantially identical to the volume of the dispensing body. Additionally, the volume of the dispensing body should take into consideration the spring travel of the dispensing body when comprised of a compressible material.

The invention thus provides a syringe that can be completely emptied of dental material so that, in principle, such syringes can be reused without running the risk that the newly introduced dental material could be contaminated by remains of old dental material. This holds true especially for the comparatively expensive, high-quality threaded syringes whereby it is understood that, if necessary, only refurbishing with the dispensing body and optionally the plunger can be performed while the syringe housing and the drive are completely reusable. Thus, the complete removal of dental material contributes to cost reduction in dental labs, respectively, dental practices.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 4.

Figure 1:
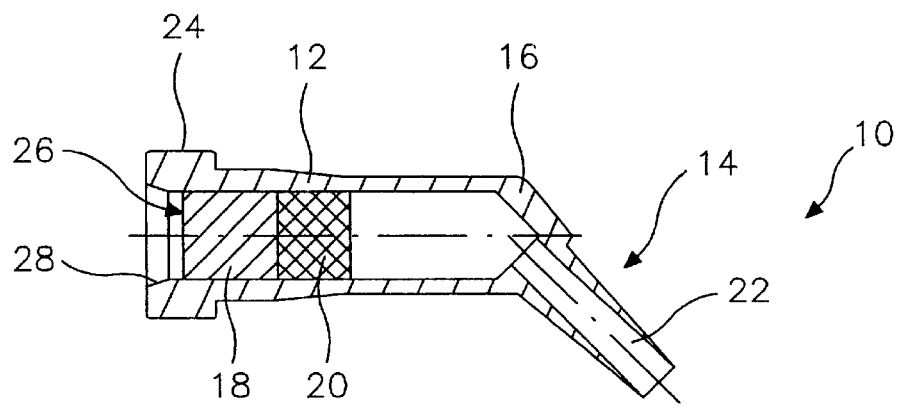
FIG. 1 is a section of the inventive syringe with the outlet member being filled, i.e., before dispensing occurs.

The syringe represented in FIG. 1 comprises a cylindrical housing 12 having connected thereto an outlet member 14 which, relative to the cylindrical housing 12, has a smaller Inner cross-section. The transition between the cylindrical housing 12 and the outlet member 14 is provided in the form of a guide cone 16.

The syringe 10 also includes a plunger 18 which consists of a dimensionally stable material. Connected to the plunger 18 is a dispensing body 20 consisting of a deformable material. Furthermore, a filling chamber 22 for the dental material is provided within the syringe whereby the syringe in the rest position is not yet filled. In order to provide for an improved accessability of tooth cavities and for improving manipulation, the outlet member 14 is positioned at an angle relative to the axes of the plunger 18 and the cylindrical housing 12.

The plunger 18 is actuatable by a non-represented push rod which is part of a syringe securing device that is also not represented.

The syringe securing device engages projections 24 at the cylindrical housing 12 of the syringe 10 while the push rod acts onto a pressure surface 27 of the plunger 18.

In the shown embodiment, the plunger 18 is a comparatively long plunger which is favorable with regard to dimensional stability. However, with respect to material savings, the plunger can be embodied so as to be substantially shorter, respectively, can have a length of only a third of its diameter. Due to the elasticity of the dispensing body 20, it acts as a sealing element so that the plunger 18 provides essentially a uniform pressure distribution at the back side of the dispensing body 20. When needed, the plunger 18 can also be realized by coating the dispensing body 20 with a dimentionally stable material.

In order to facilitate introduction, an insertion cone 28 is provided at the rearward end of the syringe 10. This insertion cone 28 allows the introduction of the dispensing body 20 and of the plunger 18, preferably formed as a unitary part, even when the dispensing body 20 in the relaxed state has a larger diameter than the inner diameter of the cylindrical housing 12.

The dispensing body 20 in the relaxed state is preferably cylindrical. If desired, in the relaxed state it can be provided so as to have a mantle surface in the shape of a flat cone. With such an embodiment the inner pressure within the area neighboring the plunger 18 is increased which improves the sealing action. Furthermore, it is possible to provide the tip of the dispensing body 20 with a rather flat cone which should have a cone angle greater than the cone angle of the guide cone 16.

Figure 2:
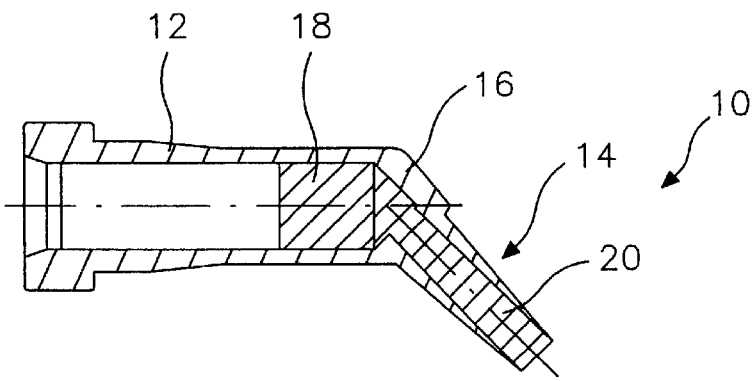
FIG. 2 shows the syringe of FIG. 1 after completion of the dispensing process.

As can be seen in FIG. 2, the dispensing body 20 is deformable to such an extent that it allows the complete removal of the dental material 22 from the syringe 20 by completely filling the entire interior space (inner volume) of the guide cone 16 and of the outlet member 14. In the shown embodiment, the outlet member 14 has a cylindrical inner shape whereby it is understood that the diameter of the outlet member 14 in a modified embodiment can also be slightly tapered.

As Can be seen in FIG. 2, the plunger 18 contacts the guide cone 16 in the position In which the dispensing body 20 completely fills the outlet socket 14. Thus, the guide cone 16 provides an abutment for the plunger 18 and a signal for the operator that a further dispensing action is not possible and the dental material contained in the syringe has been completely dispensed. As can been seen in FIG. 2, no dental material remains within the area of the guide cone 16 and of the outlet member 14. The syringe is thus completely emptied and can be disposed of as a disposable syringe.

Figure 3:
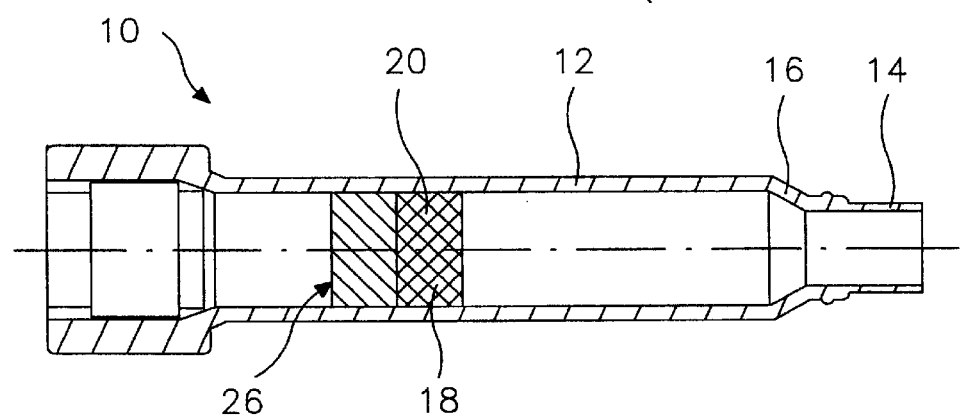
FIG. 3 shows another embodiment of the inventive syringe in the state before dispensing.
Figure 4:
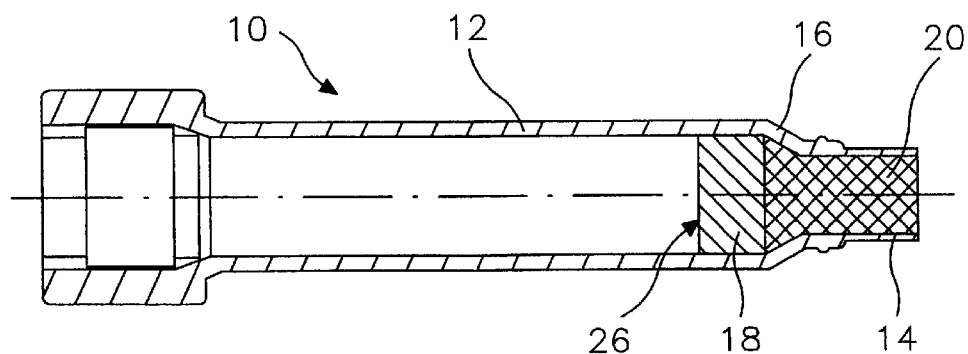
FIG. 4 shows the syringe according to FIG. 3 after dispensing.

FIG. 3 shows a further embodiment of an inventive syringe. In this embodiment, the outlet member 14 extends coaxially within the cylindrical part 12. Furthermore, the diameter difference between the outlet member 14 and the cylindrical housing 12 Is less pronounced than in the embodiment represented in FIGS. 1 and 2 of the inventive syringe 10. In the embodiment of FIG. 3, the guide cone 16 extends at a flatter cone angle than in FIG. 1 so that only a reduced deformation of the dispensing body 20 is required. The syringe 10, represented in FIG. 3 in the filled state and in FIG. 4 in the empty state, is designed for a screw actuation the elements of which are known per se and are not represented in detail in the drawings. The plunger 18 comprises a pressure surface 26 and abuts directly the dispensing body 20. The dispensing body 20 is elastically deformable and, upon introduction into the guide cone 16, compressed automatically to the diameter of the outlet member 14 as shown in FIG. 4.

Since a relatively large diameter of the outlet member 14 is provided, it Is possible, if desired, to return the plunger 18 and the dispensing body 20 connected thereto, after loosening the screw acutuation rod for the plunger, in order to refill the syringe with new dental material. Thus, a reuse of the threaded drive is possible. It is understood that it is preferred to exchange, if needed, the component comprised of the plunger and the dispensing body.

The present Invention is, of course, in no way restricted to the specific disclosure of the specification and drawings, but also encompasses any modifications within the scope of the appended claims.

What is claim is:

1. A syringe for dispensing a viscous material, said syringe comprising:
    a cylindrical housing having a first and a second end, and a large diameter cylindrical opening at the second end;
    an outlet member connected to said first end of said cylinderical housing, said outlet member having a small diameter cylindrical outlet opening;
    a deformable dispensing body slidable in said cylindrical housing from said second end to said first end for dispensing viscous material in a dispensing direction of said syringe, said deformable dispensing body capable of being deformed to such an extent that it may be inserted at least partly into said small diameter cylindrical outlet member when dispensing the viscous material so that viscous materials may be substantially completely dispensed from the syringe, said dispensing body having a dimensionally stable trailing end portion remote from said outlet member.

2. A syringe according to claim 1, further comprising a plunger connected to said trailing end for moving said deformable dispensing body within said cylindrical housing.

3. A syringe according to claim 1, wherein said deformable dispensing body is a plunger and has an outer diameter matching an inner diameter of said cylindrical housing, wherein said deformable dispensing body has a leading end for deformable insertion into said outlet member.

4. A syringe according to claim 1, wherein said outlet member tapers conically toward said outlet opening.

5. A syringe according to claim 1, wherein said outlet opening has an identical cross-section from said first end of said cylindrical housing to said outlet opening.

6. A syringe according to claim 1, wherein said outlet member has a tapering cross-section relative to said cylindrical housing.

7. A syringe according to claim 1, further comprising a guide cone, connected between said cylindrical housing and said outlet member, for guiding said deformable dispensing body into said outlet member.

8. A syringe according to claim 7, wherein said deformable dispensing body has a volume matching an inner volume of said outlet member and of said guide cone.

9. A syringe according to claim 1, further comprising a plunger for moving said deformable dispensing body within said cylindrical housing, wherein said plunger is fastened to said trailing end of said deformable dispensing body.

10. A syringe according to claim 9, wherein said plunger and said deformable dispensing body are in the form of a unitary plastic part and wherein said plunger is formed by curing or cross-linking a portion of said unitary plastic part.

11. A syringe according to claim 9, wherein said plunger is glued to said trailing end.

12. A syringe according to claim 1, wherein said trailing end comprises a guide disk forming a plunger of said syringe and providing a seal relative to said cylindrical housing.

13. A syringe according to claim 1, wherein said deformable dispensing body consists of an elastomer having a shore hardness of 10 to 90.

14. A syringe according to claim 13, wherein the shore hardness is 20 to 60.

15. A syringe according to claim 1, wherein said deformable dispensing body comprises a pointed tip in relaxed state thereof, wherein a tapering angle of said pointed tip is greater than a tapering angle of said outlet member.

16. A syringe according to claim 1, wherein said deformable dispensing body comprises a substantially nondeformable plunger and an elastic part connected to said plunger, wherein said elastic part is insertable into said outlet member for completely dispensing the viscous material from said outlet member.

17. A syringe according to claim 16, wherein said elastic part has a radial projection forming a sealing lip relative to an inner diameter of said cylindrical housing.

18. A syringe according to claim 1, wherein said outlet member is angularly positioned relative to said cylindrical housing and wherein said deformable dispensing body extends into said outlet member when said syringe is completely emptied.

19. A syringe according to claim 18, wherein said outlet member is positioned at an angle of 45° relative to said cylindrical housing.

20. A syringe according to claim 1, wherein said deformable dispensing body is a fluid-filled body.

21. A syringe according to claim 20, wherein said fluid-filled body is filled with hydrogel.

22. A syringe according to claim 1, further comprising a plunger for moving said deformable dispensing body within said cylindrical housing, wherein said deformable dispensing body is inserted into said cylindrical housing before inserting said plunger.

23. A syringe according to claim 1 in combination with a viscous material contained in said cylindrical housing.

24. A method for manufacturing a syringe for dispensing viscous material, said syringe comprising a cylindrical housing and an outlet member connected thereto, said syringe further comprising a plunger slidable in said cylindrical housing and a deformable dispensing body positioned in front of said plunger in a dispensing direction of said syringe, wherein said deformable dispensing body is provided for displacing the viscous material from said syringe and is at least partly insertable into said outlet, said method comprising the steps of:

injection molding in two steps a first layer and a second layer so as to form said deformable dispensing body, wherein said second layer is more elastic than said first layer;

positioning said deformable dispensing body in said cylindrical housing such that said second elastic layer faces said outlet member.

25. A method according to claim 24, wherein the step of injection nolding includes forming a sheet of said first and said second layers, said method further comprising the step of stamping said deformable dispensing b6dy from said sheet.

26. A method according to claim 24, further comprising the step of cross-linking said deformable dispensing body at one end for hardening said first layer.

* * * * *